United States Patent [19]

Petterson et al.

[11] Patent Number: 4,940,828

[45] Date of Patent: Jul. 10, 1990

[54] STEAM CRACKING FEED GAS SATURATION

[75] Inventors: William C. Petterson, Missouri City; Thomas A. Wells, Houston; Peter Cherish, Kingwood; Stephen W. Morgan, Spring, all of Tex.

[73] Assignee: The M. W. Kellogg Company, Houston, Tex.

[21] Appl. No.: 420,856

[22] Filed: Oct. 13, 1989

[51] Int. Cl.$^5$ ................................................. C07C 4/02
[52] U.S. Cl. ................................ 585/652; 585/648; 585/649; 585/650
[58] Field of Search ................ 585/648, 649, 650, 652

[56] References Cited

U.S. PATENT DOCUMENTS

| | | |
|---|---|---|
| 1,910,199 | 5/1933 | Brady . |
| 1,923,656 | 8/1933 | Beekley ................................. 23/212 |
| 1,988,759 | 1/1935 | Svanoe ................................. 23/212 |
| 3,230,055 | 1/1966 | Wolfrom ............................... 23/285 |
| 4,166,799 | 9/1979 | Giacobbe ............................. 252/182 |
| 4,172,857 | 10/1979 | Pavilon ................................ 585/652 |
| 4,349,358 | 9/1982 | Tarancon ................................. 55/89 |
| 4,426,278 | 1/1984 | Kosters ................................ 585/652 |
| 4,492,624 | 1/1985 | Johnson et al. ...................... 585/652 |
| 4,543,177 | 9/1985 | Murthy et al. ....................... 585/652 |
| 4,552,644 | 11/1985 | Johnson et al. ...................... 585/652 |
| 4,574,062 | 3/1986 | Weitman ............................... 261/147 |
| 4,681,603 | 7/1987 | Spangler et al. ......................... 55/27 |
| 4,705,654 | 11/1987 | Niwa et al. ........................... 261/128 |

Primary Examiner—Curtis R. Davis

[57] ABSTRACT

Dilution steam for steam cracking hydrocarbons to produce lower olefins is economically provided by saturating gaseous hydrocarbon feed with water at a temperature selected to achieve the particular steam to hydrocarbon ratio desired in the steam cracking step. Complete saturation of the feed gas is ensured by injecting the gas into the flooded portion of an indirectly heated tubular saturation zone.

3 Claims, 1 Drawing Sheet

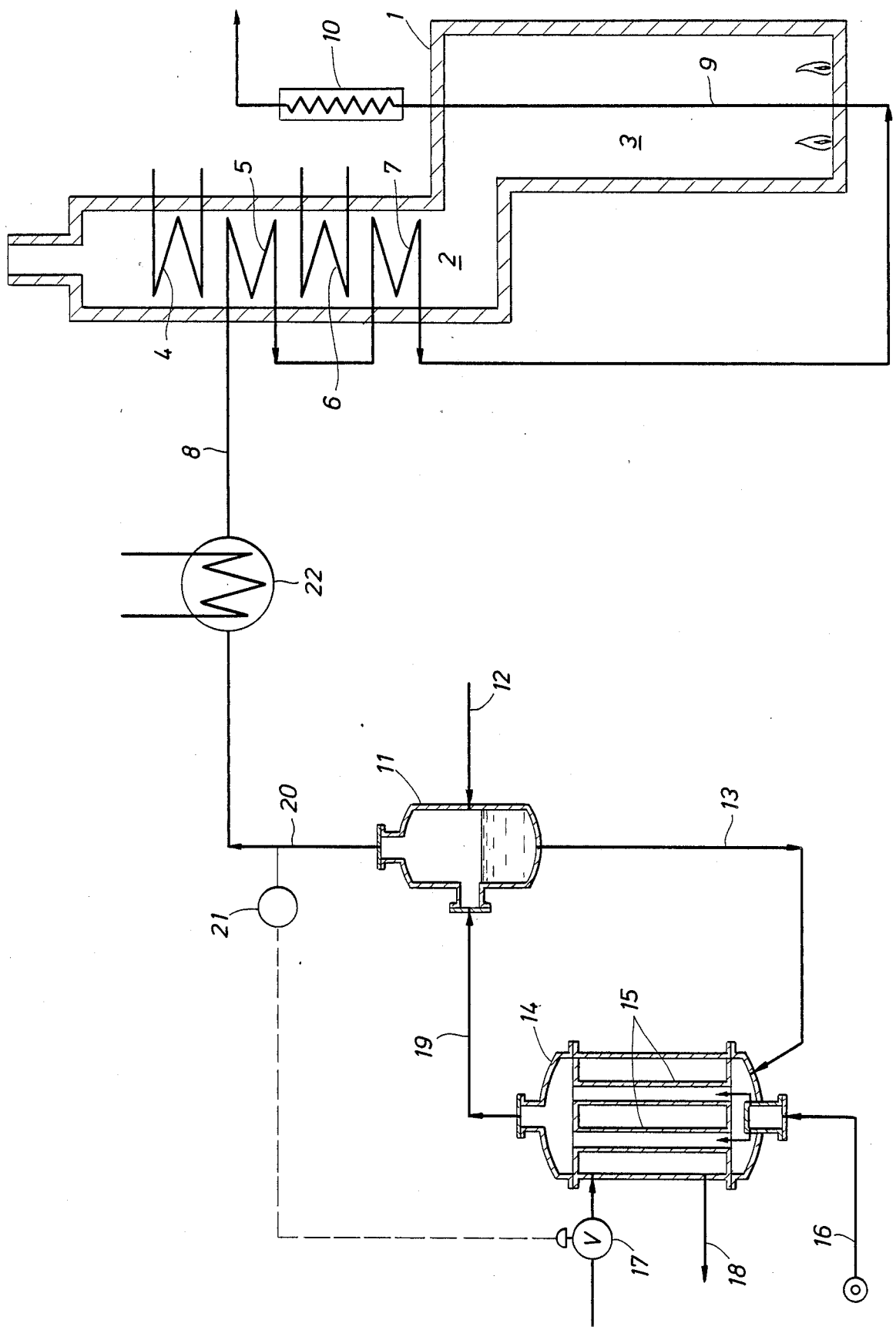

STEAM CRACKING FEED GAS SATURATION

This invention relates to steam cracking hydrocarbons for the production of lower olefins. More particularly, this invention relates to the addition of dilution steam to gaseous hydrocarbon feedstocks as well as control of the steam/hydrocarbon ratio in the resulting mixed feed which is introduced to the steam cracking furnace.

The basic process steps for production of lower olefins such as ethylene and propylene are well known and comprise high temperature steam cracking of hydrocarbons ranging from ethane to very heavy gas oil, quenching the resulting cracked gases and then further cooling them, separation of process condensate and normally liquid hydrocarbons, compression of the remaining cracked gases to elevated pressure, refrigerating the compressed gases, and multiple expansion of the refrigerated gases through a series of fractionating columns to separate product ethylene and co-products.

The steam cracking step is customarily carried out in a tubular fired furnace having a radiant section where cracking occurs and a convection section where waste heat from the radiant section is recovered by feed preheating and steam generation. Steam cracking reactions are favored by high temperature and low pressure. In commercial practice, "dilution steam" is added to the hydrocarbon feed in sufficient amount to achieve the lowest hydrocarbon partial pressure that is economically practical. Dilution steam also suppresses coke formation in the cracking tubes. Typical steam/hydrocarbon weight ratios for various feeds are:

ethane, propane; 0.3 to 1
naphtha; 0.4 to 1
gas oil; 0.6 to 1

In actual practice, the steam/hydrocarbon ratio is varied to satisfy requirements for complete vaporization of feeds and prevailing economic conditions. Lower ratios tend to reduce utility and energy consumption in an olefins plant; high ratios tend to improve yield selectivity and reduce feedstock consumption.

Dilution steam is a production cost factor because it is customarily generated from process condensate by heat exchange with high pressure steam or flue gas within the cracking furnace convection section. It is evident that dilution steam would be less costly if it could be provided by saturation of the hydrocarbon feed gas with process condensate in a manner that achieves the desired steam/hydrocarbon ratio and requires only a low level heat source having little or no economic value.

According to the invention, dilution steam for steam cracking gaseous hydrocarbons is provided and controlled by circulating water upwardly through a heated tubular saturating zone with cocurrently injected hydrocarbon feed. A two phase mixture recovered from the tubular saturating zone is separated into a water stream for recirculation and a mixed feed stream of normally gaseous hydrocarbon fully saturated with water which is introduced to a steam cracking zone without necessity for addition of supplemental steam. The composition of the mixed feed stream, that is to say the steam/hydrocarbon ratio, is controlled by choice of the operating saturation temperature selected in the saturation system. Injection of hydrocarbon feed gas into the lower, flooded portion of the tubular saturating zone ensures full saturation of gas at the water temperature. The water temperature is maintained by controlling the rate of indirect heat exchange in the tubular saturating zone.

The tubular saturating zone is suitably provided by a vertical shell and tube heat exchanger arranged for circulation of water, preferably, process condensate, upwardly through the tubes and is further arranged for upward injection of gaseous hydrocarbon feed into the tubes cocurrently with the circulating water. The water and gas within the zone are heated at a variably controlled rate by indirect heat exchange with a heating fluid.

A two phase, equilibrium mixture of water and water-saturated hydrocarbon feed is recovered from the saturating zone and introduced to a vapor/liquid separation zone having a static liquid pressure greater than that of the saturating zone. Conveniently, the separator is physically located above the saturating heat exchanger.

Upward flow of water through the saturating zone is induced by convective circulation, commonly referred to as thermosiphon circulation, resulting from heat input to the zone. This circulation is augmented by upward gas injection into the saturating zone and may optionally be further augmented by a circulating pump.

Vapor separated from the two phase mixture is a mixed feed stream comprised of the gaseous hydrocarbon fully saturated with water at the temperature of the stream. This temperature is selected as the saturation temperature for a mixed feed stream having the desired steam/hydrocarbon ratio and is maintained by control of heating fluid to the tubular saturating zone.

Since the mixed feed stream will be further preheated in, usually, convection coils of the steam cracking furnace, the mixed feed stream should be free of hydrocarbon liquid in order to avoid problems associated with heating two phase mixtures in furnace coils. Heavier hydrocarbon feeds such as naphthas can be maintained in a gaseous state throughout the saturation system by maintaining the system at higher temperatures, however, higher level heat sources are required which, correspondingly, decrease economic incentive for use of the described saturation system. Accordingly, we prefer to employ steam as the heating fluid at a pressure between 0 and 7.2 bar which will permit selection of the controlling temperature of the mixed feed vapor stream in the range between 88° C. and 160° C. At customary mixed feed stream pressures in the range from 2.7 bar to 8.3 bar, this range of saturation temperatures will permit achievement of steam to hydrocarbon weight ratios in the range between 0.15 and 0.6.

Referring now to the drawing, a known steam cracking furnace 1 having convective heating section 2 and radiant heating section 3 is employed to crack hydrocarbons to ethylene and other desired products. The convection section 2 is equipped with coils 4, 5, 6, 7 which recover waste heat from the furnace.

In the particular furnace arrangement illustrated, a mixed feed stream 8 at 5.5 bar and containing dilution steam and propane in a weight ratio of 0.3 to 1 is heated to incipient cracking temperature in furnace coils 5 and 7 and introduced to cracking tubes 9 (only single tube is shown). Cracked gases from tubes 9 are quickly cooled in quench exchanger 10 and then introduced to a product separation system not shown.

In accordance with the invention, dilution steam condensate separated from cracked gases is introduced to vapor/liquid separator 11 through line 12 as make-up water to the hydrocarbon feed gas saturation system.

Water from separator 11 flows downwardly through line 13, into the flooded bottom head of heat exchanger 14, and upwardly through the tubular saturating zone formed by tubes 15. Propane feed is introduced to the system by line 16 and injected into tubes 15 where it flows cocurrently upward with and is saturated by the water introduced through line 13. The water and propane mixture within is heated by indirect heat exchange at a variably controlled rate with steam at 3.5 bar introduced through control valve 17. Steam condensate is removed from the shell side of heat exchanger 14 through line 18.

A two phase, equilibrium mixture of water and propane is recovered from the top head of heat exchanger 14 and introduced through line 19 to vapor/liquid separator 11 from which a mixed feed stream of fully water-saturated propane is recovered through line 20. The mixed feed stream has the desired steam/propane weight ratio of 0.3 to 1 because of its full saturation with water at the temperature and pressure conditions existing in the tubular saturating zone which, in turn, are controlled by the system pressure and the temperature selected at controller 21. In this example in which mixed feed stream 8 is at 5.5 bar, the temperature of the mixed feed stream 20 leaving separator 11 required to fully saturate the propane at the desired steam/propane ratio is 130° C. Steam flow through valve 17 is therefore controlled by temperature controller 21 to maintain the selected 130° C. temperature. The mixed feed stream is then optionally preheated in heat exchanger 22 and further heated to incipient cracking temperature of 650° C. in furnace coils 5 and 7 prior to introduction to cracking tubes 9. Since the desired steam/propane ratio of the mixed feed stream is achieved in the feed gas saturation system, no supplemental steam is added to the stream.

We claim:
1. A method of controlling the dilution steam for steam cracking gaseous hydrocarbons which comprises:
   (a) circulating water upwardly through a tubular saturating zone and heating the water therein at a variably controlled rate by indirect heat exchange with a heating fluid;
   (b) injecting a gaseous hydrocarbon feed into a lower, flooded portion of the tubular saturating zone in cocurrent flow with the circulating water;
   (c) recovering a two phase, equilibrium mixture comprised of water and water-saturated hydrocarbon feed from the tubular saturation zone;
   (d) introducing the two phase, equilibrium mixture to a separation zone having a static liquid pressure greater than that of the tubular saturation zone;
   (e) recovering a water stream from the separation zone and recirculating the recovered water stream to the tubular saturating zone;
   (f) recovering a mixed feed vapor stream of gaseous hydrocarbon fully saturated with water from the separation zone;
   (g) controlling the rate of indirect heat exchange in the tubular saturation zone by selecting a controlling temperature of the mixed feed vapor stream; and
   (h) introducing the mixed feed vapor stream to a steam cracking zone.

2. The method of claim 1 wherein the heating fluid is steam at a pressure between 0 and 7.2 bar, the pressure of the mixed feed vapor stream is between 2.7 bar and 8.3 bar, and the selected controlling temperature of the mixed feed vapor stream is between 88° C. and 160° C.

3. The method of claim 1 wherein the water flows through the tubular saturating zone by thermosiphon circulation.

* * * * *